US011160497B1

(12) United States Patent
Hayman

(10) Patent No.: US 11,160,497 B1
(45) Date of Patent: Nov. 2, 2021

(54) SOFTWARE CONFIGURATION FOR VIRTUAL SKINCARE ASSESSMENT AND VIRTUAL CUES

(71) Applicant: Hillary Hayman, Los Angeles, CA (US)

(72) Inventor: Hillary Hayman, Los Angeles, CA (US)

(73) Assignee: ELYSE ENTERPRISES LLC, Los Angeles, CA (US)

( * ) Notice: Subject to any disclaimer, the term of this patent is extended or adjusted under 35 U.S.C. 154(b) by 0 days.

(21) Appl. No.: 16/931,182

(22) Filed: Jul. 16, 2020

(51) Int. Cl.
*A61B 5/00* (2006.01)
*G06F 3/0484* (2013.01)
(Continued)

(52) U.S. Cl.
CPC .......... *A61B 5/4848* (2013.01); *A45D 44/00* (2013.01); *A61B 5/0077* (2013.01); *A61B 5/442* (2013.01);
(Continued)

(58) Field of Classification Search
CPC ..... A61B 5/4848; A61B 5/0077; A61B 5/442; A61B 5/486; A61B 5/7405; A61B 5/7435; A61B 5/7475; A61B 2576/02; G16H 50/30; G16H 50/20; A45D 44/00; A45D 2044/007; A61H 15/00; A61H 2201/1695; G06F 3/0482; G06F 3/04847; G06K 9/00335; G06Q 30/0631; G06T 7/0012;
(Continued)

(56) References Cited

U.S. PATENT DOCUMENTS 8,376,984 B2   2/2013   James
8,858,312 B1 * 10/2014  Ward ...................... A63F 13/20
                                                             463/7
(Continued)

OTHER PUBLICATIONS

Clemetoni, Matteo, et al. "Photodynamic Photorejuvenation of the Face with a Combination of Microneedling, Red Light and Broadband Pulsed Light" ("Clementoni") (Year: 2010).*

(Continued)

*Primary Examiner* — James T Tsai
(74) *Attorney, Agent, or Firm* — Concept IP LLP; Pejman Yedidsion

(57) ABSTRACT

A software configuration generates, with a processor, a graphical user interface that renders a menu of a plurality of selection indicia. The plurality of selection indicia includes a skincare rejuvenation area indicium, a skincare assessment indicium, and a skincare interactive cue indicium. Furthermore, the software configuration receives, with the processor, a first user input corresponding to a skincare rejuvenation area associated with the skincare rejuvenation area indicium. Moreover, the software configuration receives, with the processor, a second user input corresponding to the skincare assessment indicium to initiate a skincare assessment based on the skincare rejuvenation area. Furthermore, the software configuration performs, with an image capture device, an image capture of the skincare rejuvenation area. Additionally, the software configuration performs, with the processor, an image analysis of the image capture with one or more previous image captures captured by the image capture device.

18 Claims, 12 Drawing Sheets

(51) Int. Cl.
*G06T 7/00* (2017.01)
*G06K 9/00* (2006.01)
*G16H 50/30* (2018.01)
*G16H 50/20* (2018.01)
*G06Q 30/06* (2012.01)
*A61H 15/00* (2006.01)
*A45D 44/00* (2006.01)
*G09B 19/00* (2006.01)
*G06F 3/0482* (2013.01)

(52) U.S. Cl.
CPC ............ *A61B 5/486* (2013.01); *A61B 5/7405* (2013.01); *A61B 5/7435* (2013.01); *A61B 5/7475* (2013.01); *A61H 15/00* (2013.01); *G06F 3/0482* (2013.01); *G06F 3/04847* (2013.01); *G06K 9/00335* (2013.01); *G06Q 30/0631* (2013.01); *G06T 7/0012* (2013.01); *G09B 19/003* (2013.01); *G16H 50/20* (2018.01); *G16H 50/30* (2018.01); *A45D 2044/007* (2013.01); *A61B 2576/02* (2013.01); *A61H 2201/1695* (2013.01); *G06T 2207/10016* (2013.01); *G06T 2207/30088* (2013.01)

(58) Field of Classification Search
CPC   G06T 2207/10016; G06T 2207/30088; G09B 19/003
See application file for complete search history.

(56) References Cited

U.S. PATENT DOCUMENTS

| | | | | |
|---|---|---|---|---|
| 10,096,122 | B1 * | 10/2018 | Agrawal | G06T 7/11 |
| 10,438,265 | B1 * | 10/2019 | Brown, III | G06Q 30/0631 |
| 10,485,755 | B1 * | 11/2019 | Cheng | A61K 9/0021 |
| 2003/0065526 | A1 * | 4/2003 | Giacchetti | G06T 11/00 |
| | | | | 382/276 |
| 2005/0154381 | A1 * | 7/2005 | Altshuler | A61B 18/20 |
| | | | | 606/9 |
| 2011/0201900 | A1 * | 8/2011 | Zhang | G16H 15/00 |
| | | | | 600/300 |
| 2014/0126787 | A1 * | 5/2014 | Zuhlke Kimball | G06T 7/0012 |
| | | | | 382/128 |
| 2015/0339757 | A1 * | 11/2015 | Aarabi | G06Q 30/06 |
| | | | | 705/12 |
| 2016/0210764 | A1 * | 7/2016 | Gomi | A45D 44/00 |
| 2016/0279401 | A1 * | 9/2016 | Schwab | A61L 31/042 |
| 2017/0256084 | A1 * | 9/2017 | Iglehart | G06K 9/00221 |
| 2017/0340267 | A1 * | 11/2017 | Shen | A61B 5/749 |
| 2019/0192065 | A1 * | 6/2019 | Nyambi | A61Q 19/00 |
| 2020/0196736 | A1 * | 6/2020 | Stanley | G06T 7/60 |
| 2021/0142890 | A1 * | 5/2021 | Adiri | G16H 15/00 |

OTHER PUBLICATIONS

Tina Alster, et al., "Microneedling: A Review and Practical Guide," Dermatol Surg. 2017;0:1-8; (Year: 2017).*

Kamila Zdunska, et al. "Is skin microneedling a good alternative method of various skin defects removal," Dermatologic Therapy. 2018;31:e12714. (Year: 2018).*

* cited by examiner

SOFTWARE CONFIGURATION FOR VIRTUAL SKINCARE ASSESSMENT AND VIRTUAL CUES

BACKGROUND

1. Field

This disclosure generally relates to skincare assessments. More particularly, the disclosure relates to a software configuration for assessing the efficacy of skincare systems.

2. General Background

Skincare products abound the shelves of brick-and-mortar stores, as well as the digital footprints of e-commerce platforms. Many of the product manufacturers of these products make lofty claims about the efficacy of their products, yet so many of these products do not come close to meeting the expectations provided to customers. And when customers contact customer support representatives, a common answer is that the customer must be applying the product to his or her skin incorrectly. This reason may be a factor in some instances, but product inefficacy is likely a major contributing factor in a large number of instances. Ultimately, the problem often lies with the product itself, rather than the way that the manner in which the product is being used by the product.

Yet, skincare users are willing to continue using many skincare products in the hope of finding something that works for them; oftentimes trying dozens of different products. And for some users, skincare plays far more of an important role than minor aesthetic enhancements. For example, some users have suffered from burns, scars, and disfiguration.

Accordingly, current skincare approaches are not effective in detecting skincare treatment effectiveness or accuracy.

SUMMARY

In one embodiment, a computer program product comprises a non-transitory computer readable storage that has a computer readable program stored thereon. When executed on a computer, the computer readable program causes the computer to generate, with a processor, a graphical user interface that renders a menu of a plurality of selection indicia. The plurality of selection indicia includes a skincare rejuvenation area indicium, a skincare assessment indicium, and a skincare interactive cue indicium. Furthermore, the computer is caused to receive, with the processor, a first user input corresponding to a skincare rejuvenation area associated with the skincare rejuvenation area indicium. Moreover, the computer is caused to receive, with the processor, a second user input corresponding to the skincare assessment indicium to initiate a skincare assessment based on the skincare rejuvenation area. The computer is caused to perform, with an image capture device, an image capture of the skincare rejuvenation area. Additionally, the computer is caused to perform, with the processor, an image analysis of the image capture with one or more previous image captures captured by the image capture device. Also, the computer is caused to determine, with the processor, that one or more metrics associated with the skincare rejuvenation area lack improvement in excess of a predetermined improvement threshold. Finally, the computer is caused to generate, with the processor based on the determination, one or more virtual cues that indicate visual movements during usage by the user of a skincare treatment process. The virtual cues are overlaid over an image of the user displayed by the graphical user interface.

The skincare treatment process may include three steps. Firstly, the skincare treatment process performs, with a derma roller, a plurality of movements along an area of intended rejuvenation of a human user. Secondly, the skincare treatment process applies, subsequent to the derma roller performance, a chemical compound to one or more patches of skin at the area of intended rejuvenation. Finally, the skincare treatment process emits, subsequent to the application of the chemical compound, light toward the area of intended rejuvenation. The skincare treatment process may be customized to a user based on a variety of factors (e.g., area of intended rejuvenation, age, skin sensitivity, or the like).

BRIEF DESCRIPTION OF THE DRAWINGS

The above-mentioned features of the present disclosure will become more apparent with reference to the following description taken in conjunction with the accompanying drawings wherein like reference numerals denote like elements and in which.

DETAILED DESCRIPTION

A software configuration (e.g., a software "app") is provided for providing a virtual skincare assessment and virtual cues. In essence, a computing device (e.g., smartphone, tablet device, laptop computer, personal computer, smartwatch, etc.) may operate the software configuration to assess the efficacy of a skincare system, treatment, or product. Without the need to go to a plastic surgeon's office, a dermatologist's office, or any other medical environment, the user is able to assess the efficacy of a particular skincare product, system, or treatment from anywhere in which online access is available.

Figure 1:
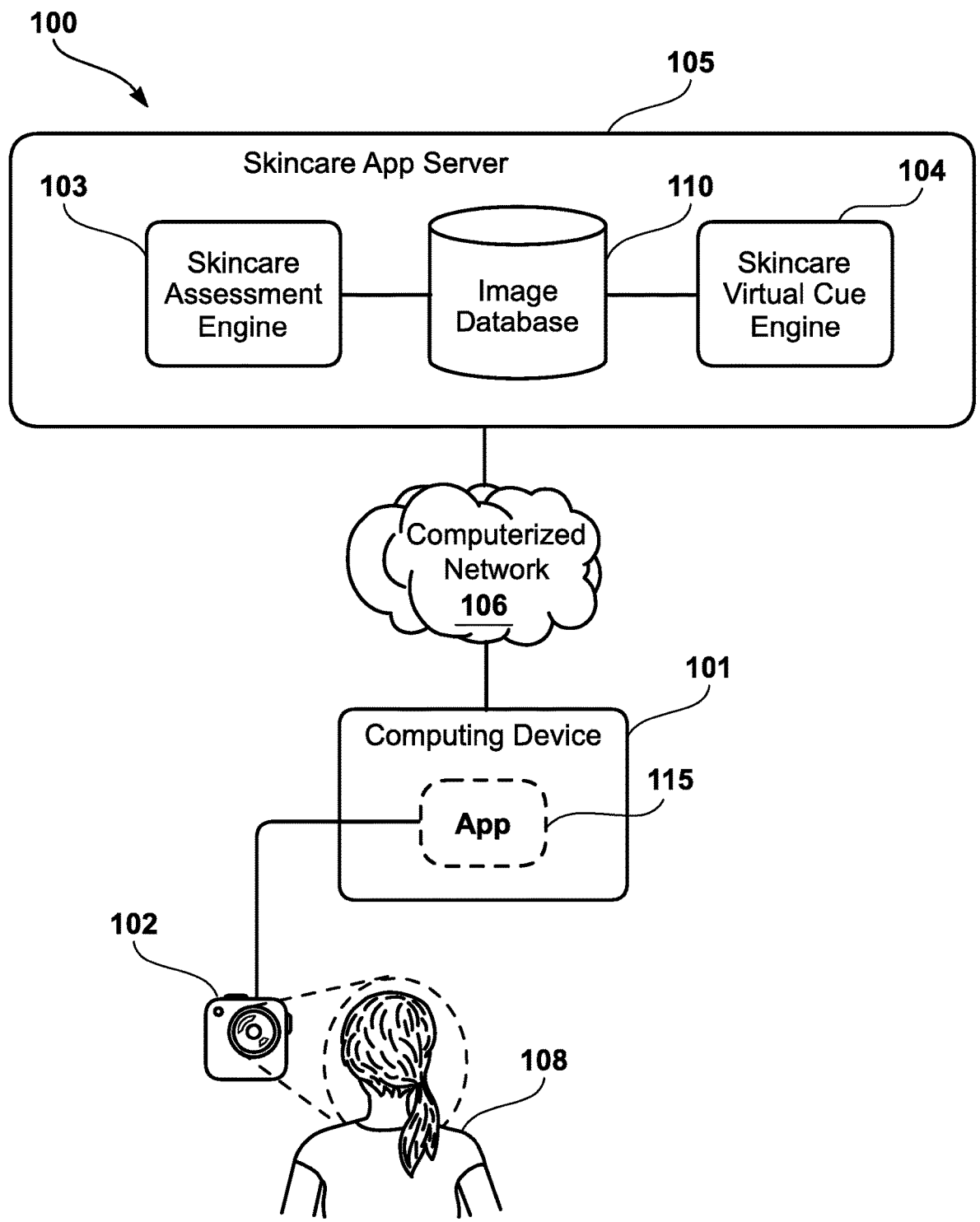
FIG. 1 illustrates a cloud-based virtual skincare assessment and virtual cue system.

FIG. 1 illustrates a cloud-based virtual skincare assessment and virtual cue system 100. In particular, the cloud-based virtual skincare assessment and virtual cue system 100 has a skincare app server 105, which may establish a software configuration 115 (e.g., an app) that is remotely accessible by a user 108 via a computing device 101 (e.g., smartphone, tablet device, smartwatch, laptop computer, personal computer, kiosk, etc.). Accordingly, instead of having to go to a physical office of a skincare professional (dermatologist, plastic surgeon, esthetician, etc.), the user 108 may utilize the app 115 to automatically assess the efficacy of a particular skincare treatment process, and the products associated therewith.

For instance, the skincare app server 105 may have a skincare assessment engine 103, which automatically assesses the efficacy of a particular skincare process, and associated products, on the skin of the particular user 108 utilizing the computing device 101; to accomplish this, the skincare app server 105 first receives, via a computerized network 106, images associated with a particular area of skincare rejuvenation (e.g., skin around the eyes, cheeks, jaw, neck, etc.) captured by an image capture device 102, which is in operable communication with the computing device 101. The image capture device 102 may be integrated within the computing device 101, or may be a separate device that communicates with the computing device 101. Based on a predetermined efficacy threshold (e.g., twenty percent improvement, although other percentages may be utilized instead), the skincare assessment engine 103 performs an image analysis to compare images of the skincare rejuvenation area. For example, the skincare assessment engine 103 may identify an area of intended rejuvenation such as a laugh line. In one embodiment, a user input (e.g., menu selection, virtual selection drawn via a touch interface around the area of rejuvenation, etc.) specifically selects the area of intended rejuvenation; whereas, in another embodiment, the skincare app server 105 automatically determines the area of intended rejuvenation by detecting areas in which the skin of the user 108 can be improved. From image capture to image capture, the skincare assessment engine 103 may locate the intended area of skincare rejuvenation (i.e., by detecting reference objects (e.g., nose, ears, etc.) and measuring the same location therefrom). In one embodiment, the skincare assessment engine 103 may then analyze each of the pixels within a given area (e.g., a geometrically shaped area of a predetermined size) for comparison with pixels in similarly situated areas in other images. By detecting various changes (e.g., changes in discoloration, opacity, density, pore size, etc.) of the corresponding pixels, the skincare assessment engine 103 may determine improvements or regressions of a user's skin over various time intervals. In another embodiment, to improve the efficiency of the computational analysis performed for the image analysis, and thereby improve the real-time, or substantially real-time, assessment of the skin of the user 108, the skincare assessment engine 103 may analyze only a probabilistically relevant portion of the intended rejuvenation area. For example, the skincare assessment engine 103 may filter out portions that have improved over a predetermined improvement threshold (e.g., a portion of a wrinkle that has already improved may not need to be analyzed again.). By reducing the number of pixels that are analyzed, the skincare assessment engine 103 improves the processing speed at which a user may obtain a skincare assessment of a particular skincare process, and corresponding products. This instant feedback allows the user 108 to avoid the inconvenience and expense of travelling to a skincare practitioner's office, while also allowing the user 108 to determine if the skincare process and corresponding products are working for him or her.

And if the if the skincare process and corresponding products are not working on the user 108, the skincare app server 105 invokes a skincare virtual cue engine 104 to guide the user 108 via one or more virtual cues (e.g., arrows) to improve performance of the process and use of the products. Accordingly, in real-time, or substantially real-time, the user 108 is able to use the computing device 101 to view and learn how to improve the efficacy of the skincare process and corresponding products for his or her particular skin. This customized approach allows the user 108 to obtain assessment and guidance anywhere that online access is available.

Figure 2:
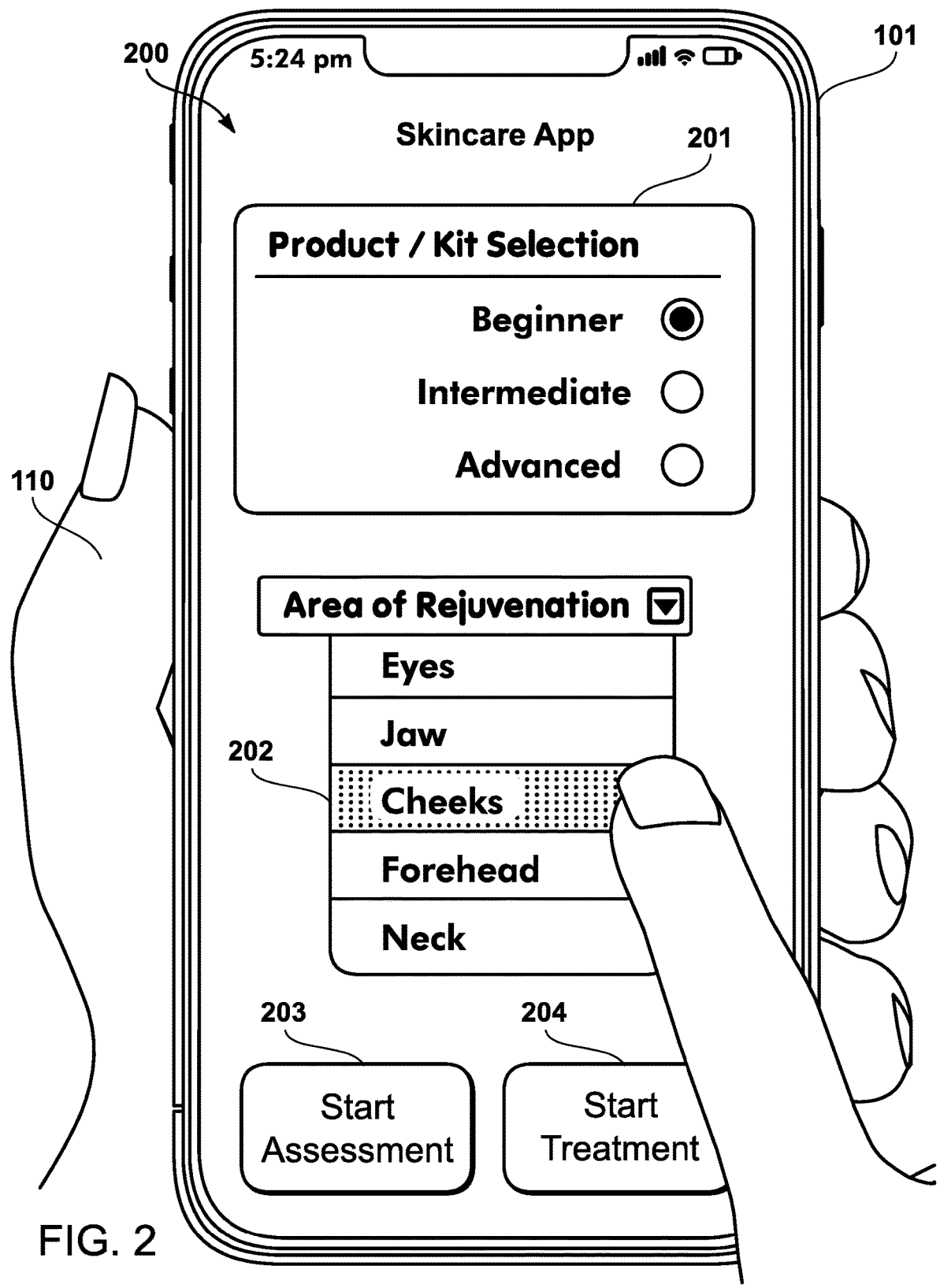
FIG. 2 illustrates an example of the computing device being a smartphone that renders a graphical use interface ("GUI") for operation of the app.

FIG. 2 illustrates an example of the computing device 101 being a smartphone that renders a GUI 200 for operation of the app 115, illustrated in FIG. 1. In one embodiment, the GUI 200 has various menus, or other input modalities, to receive user selections from the user 108. For example, the GUI 200 may have a skincare product/kit selection menu 201 that allows the user 108 to select different products, or kits thereof with different progression levels (e.g., beginner, intermediate, and advanced) on which to perform the skincare assessment. Furthermore, the GUI 200 may have an area of rejuvenation menu 202, which allows the user 108 to select the area of rejuvenation (e.g., eyes, jaw, cheeks, etc.) on which the skincare assessment should be performed. In other words, the user 108 may select a particular area of focus for skincare assessment. (As an alternative, the menus and user selections described herein may be provided via audio emissions.) For example, one particular skincare product may have significant efficacy in the cheek area, but may lack much efficacy in the jawline area. As a result, the GUI 200 allows the user 108 to determine which processes and products work for specific areas of the skin; rather than an overall assessment that is devoid of the understanding that certain processes and products may work better in different areas of the anatomy (e.g., certain anatomical structures have thicker skin than others).

Additionally, the GUI 200 may have various indicia for invoking the software configuration 115. For example, the GUI 200 may have a start assessment indicium 203 that may be invoked by the user 108 to invoke the skincare assessment. The user 108 may then be prompted to perform image capture of himself or herself, particularly with respect to the intended area of rejuvenation. In one embodiment, the skincare assessment engine 103 is configured to automatically prompt the user 108 when to perform the image capture at predetermined time intervals (e.g., a weekly basis). For example, an alert may be sent to the user 108 via the software configuration 115 as a reminder to perform the three-step skincare treatment process at a given time interval, and potentially perform an image capture to track progress. Furthermore, to ensure that the user 108 waits the minimum amount of time for treatment, the software configuration 115 may automatically prevent the user 108 from performing the skincare assessment until the next designated time interval through an automatic lockout.

Additionally, the GUI 200 may have a start treatment indicium 204 that the user 108 may invoke to initiate interactive monitoring and cue generation during the skincare treatment process performed by the user 108. Accordingly, the software configuration may be a companion app that facilitates performance of the skincare treatment process. The companion app, through the image capture device 102, may determine in real-time (measured during performance of the process by the user 108), or substantially real-time, whether or not the user 108 is performing the skincare treatment process properly. For example, the companion app may determine if the user 108 is moving a particular device in the correct direction. On-the-fly image analysis may be performed to compare the movements (direction of movements, length of movements, etc.) of the device with baseline movements, and any deviation outside of a predetermined tolerance threshold may invoke a virtual cue, such as an arrow indicating to the user 108 how to correct the movement. As another example, the companion app may determine how much pressure is being applied to the skin (e.g., via infrared emission measurements or other form of light emission measurements) to determine if the user 108 is applying enough, or too much, pressure to obtain effective results, and provide visual or audio cues to guide the user with respect to proper performance.

Figure 3A:
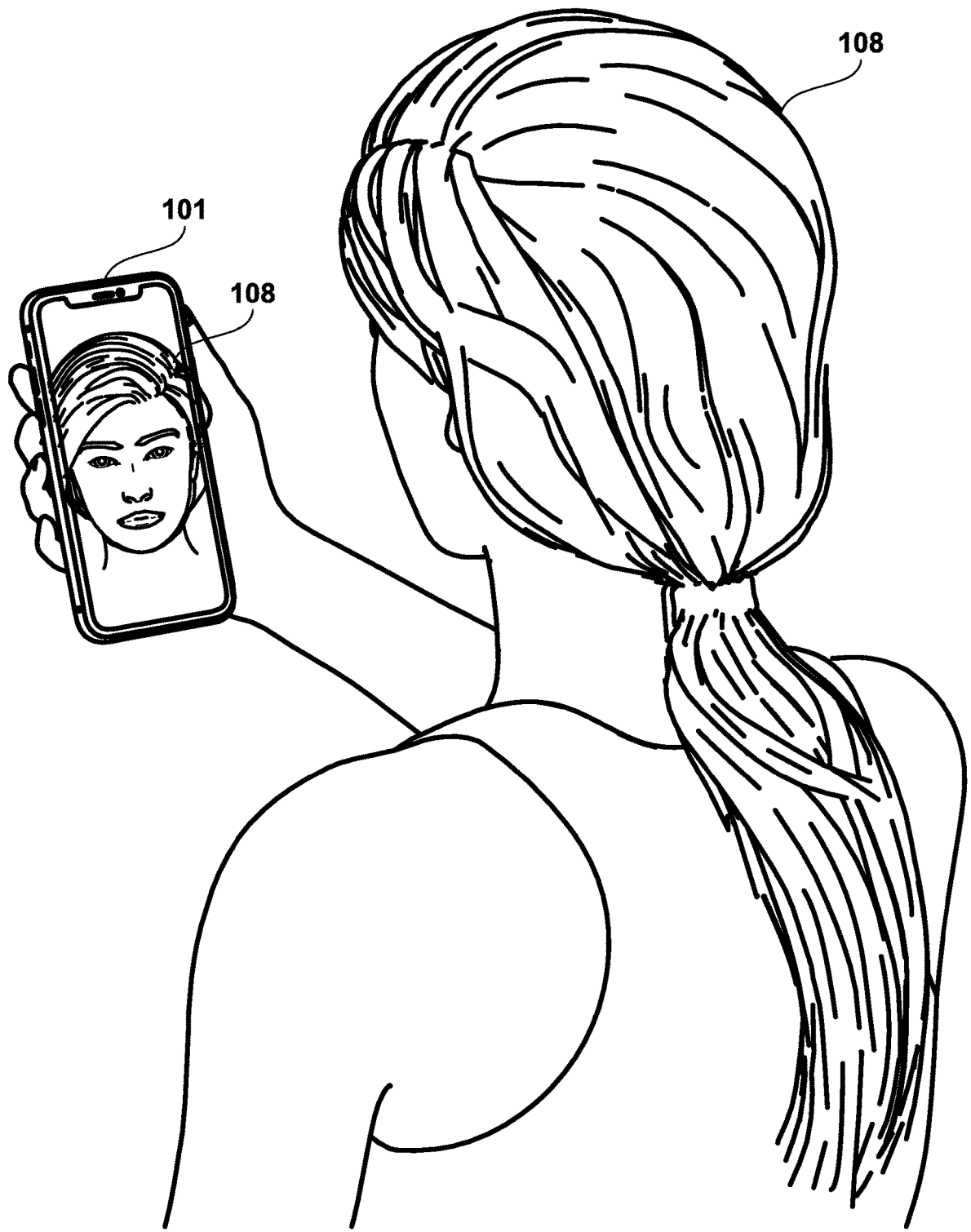
FIG. 3A illustrates the user holding the smartphone to perform image capture of herself.
Figure 3B:
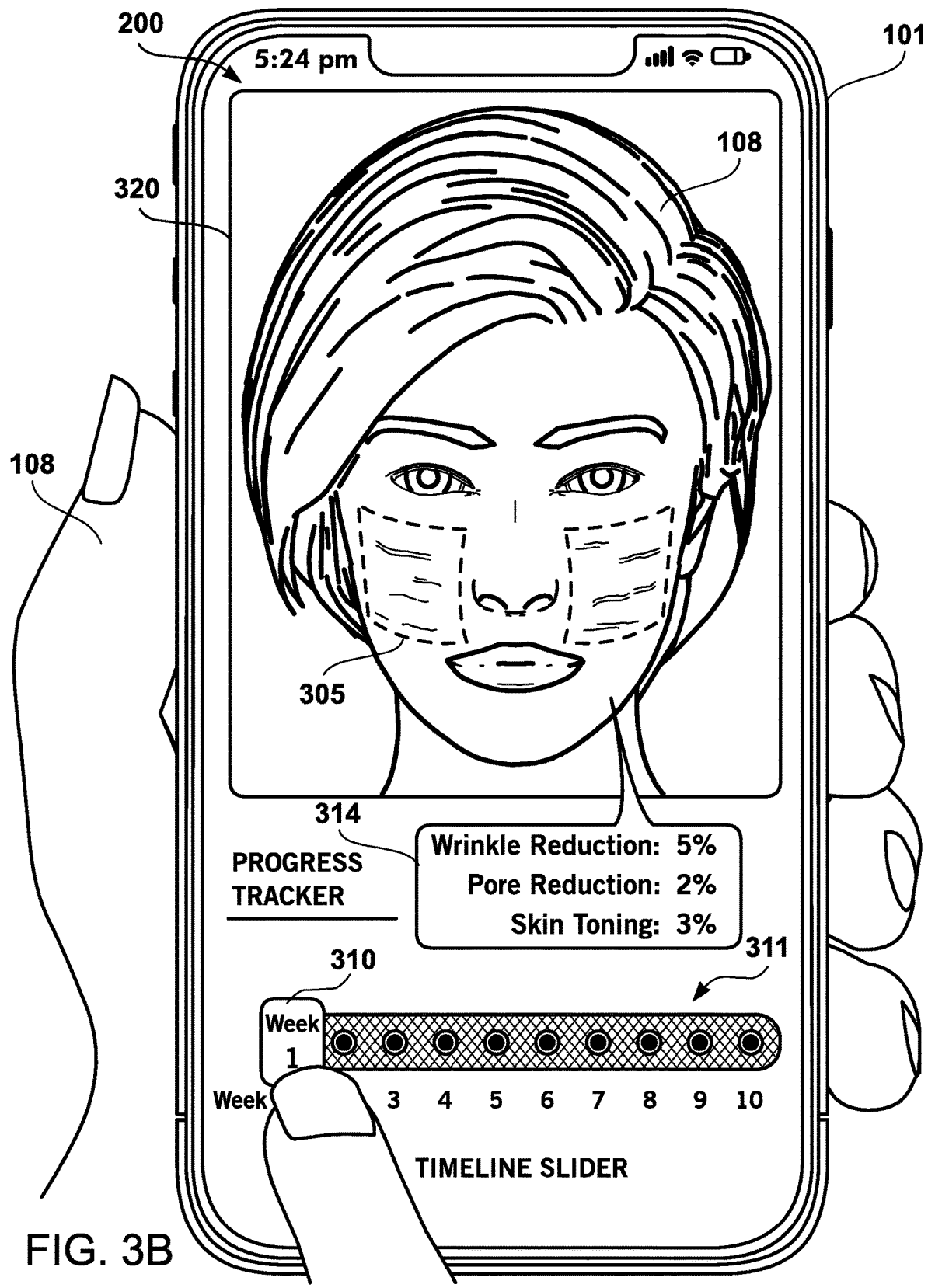
FIG. 3B illustrates a progression-based slider that allows the user to slide to a previous image of the intended are of rejuvenation.
Figure 3C:
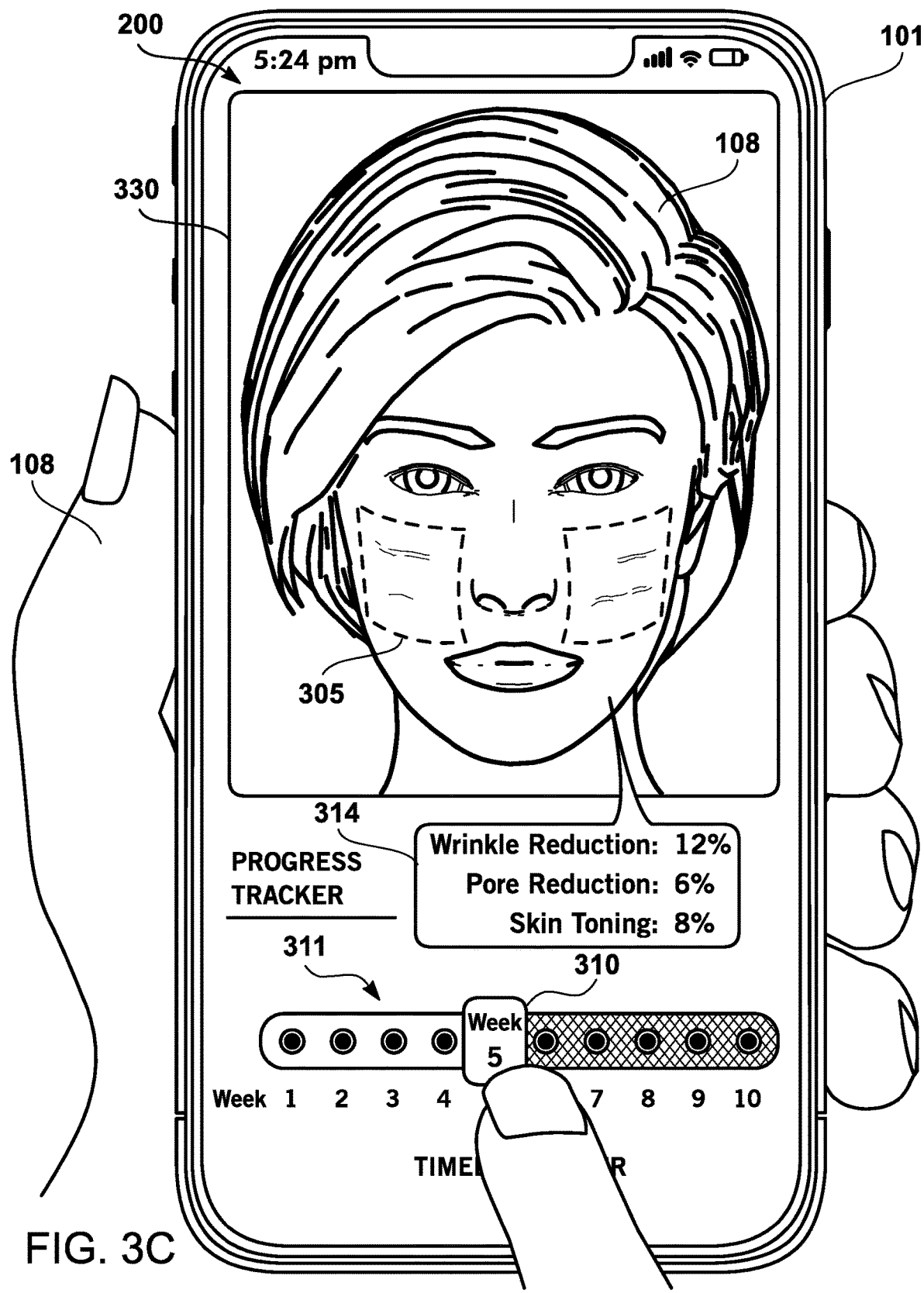
FIG. 3C illustrates the user advancing through the progression-based slider to another image to view the progress.
Figure 3D:
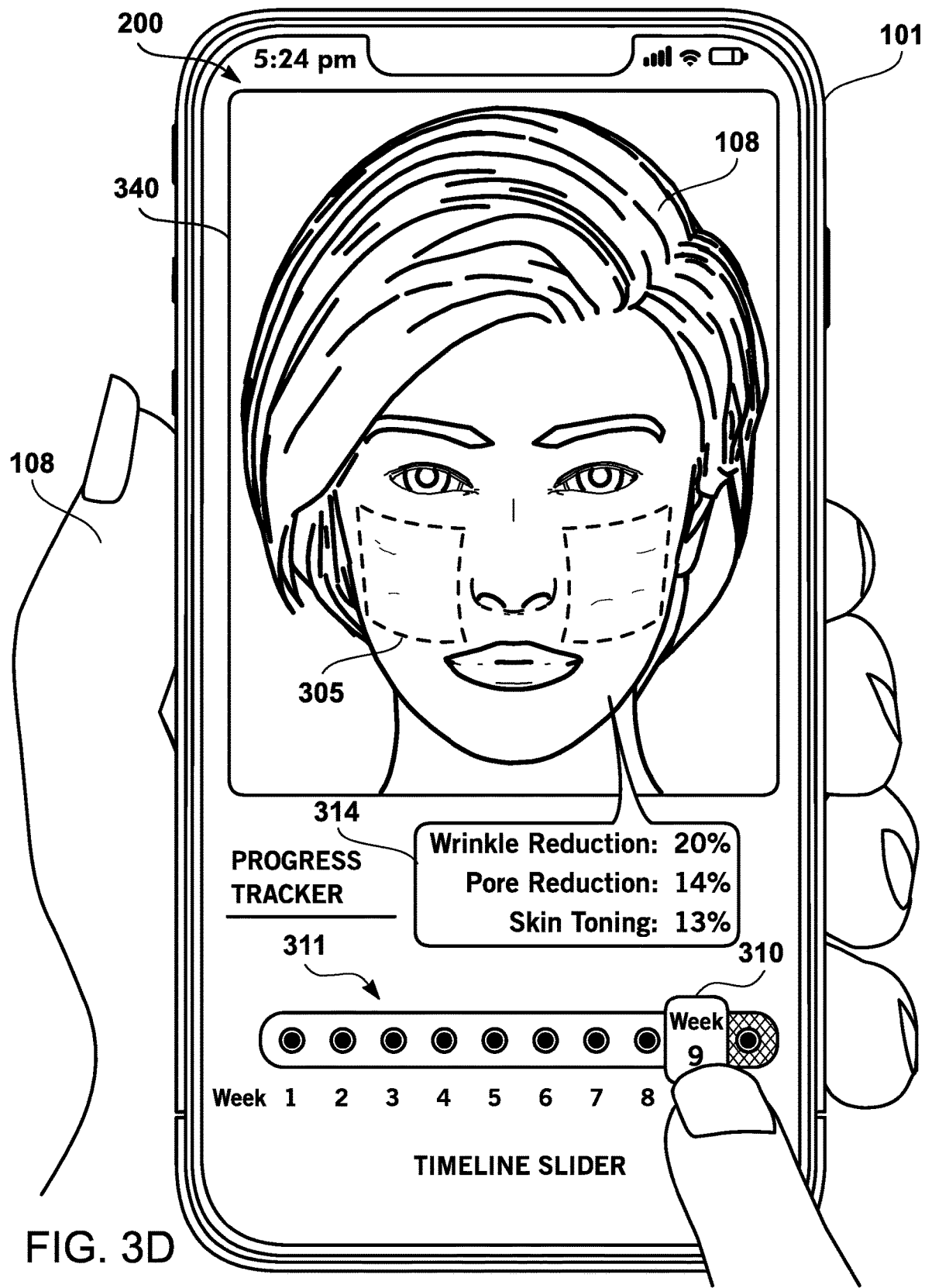
FIG. 3D illustrates the user advancing to the most recent image.

FIGS. 3A-3D illustrate the GUI 200 performing a skincare assessment after the user 108 selects the start assessment indicium 204, or provides another input (e.g., voice command, gesture, etc.) to invoke the skincare assessment. In particular, FIG. 3A illustrates the user 108 holding the smartphone 101 to perform image capture of herself. The image that is captured by the image capture device 102 is analyzed in comparison with previously captured images to provide the user 108 with feedback as to progress or lack of progress. In one embodiment, as illustrated in FIG. 3B, a progression-based slider 310 allows the user 108 to slide to a previous image 320 of the intended area of rejuvenation 305 along a virtual timeline 311, which corresponds to a plurality of time increments in between treatments. In one embodiment, the plurality of time increments may be fixed, as provided for by the particular skincare treatment product or service; such time interval may be automatically determined by the skincare app server 105 or provided via a user input from the user 108. A skincare metrics window 314 may be displayed within the GUI 200 to provide various metrics (e.g., eye wrinkle reduction, cheek wrinkle reduction, and facial pore reduction) associated with each image displayed in proximity to the corresponding time increment along the virtual timeline 311. Furthermore, as illustrated in FIG. 3C, the user 108 may advance through the virtual timeline 310 with the progression-based slider 310 to another image 330 to view the progress. The skincare metrics window 314 may be dynamically updated to reflect the particular metrics associated with a given image. Finally, as illustrated in FIG. 3D, the user 108 may advance to the most recent image 340. Accordingly, the user 108 is able to view both visual progression and data analytics metrics to assess whether a particular skincare treatment process is effective for that particular user 108 at that particular area of intended skincare rejuvenation 305.

The skincare software configuration described herein may be utilized to verify the efficacy of a multitude of particular skincare products and services. As an example of a skincare treatment process that may be utilized in conjunction with the skincare software configuration, a three-step process provides users with skincare rejuvenation that mimics plastic surgery results, without users having to undergo conventional plastic surgery procedures within a plastic surgeon's office. By way of contrast, the three-step process may be performed from the convenience of one's own home, or other place of comfort.

In particular, the three-step process has been discovered to yield results that were not readily predictable; such results mimic the effects of various plastic surgery procedures (e.g., facelifts, jaw lifts, neck lifts, forehead lifts, lower eyelid blepharoplasty, and the like) without a user having to undergo a plastic surgery procedure at the office of a medical practitioner. In essence, the three-step process includes application of various invasive and non-invasive devices/ products according to particular parameters to mimic plastic surgery results. Firstly, the three-step process includes usage of a derma roller in an area of intended rejuvenation. Particular needle lengths and movement of the derma roller has been discovered to maximize skin rejuvenation. Secondly, a chemical compound containing vitamin $A_1$ (e.g., Retinol) is applied to the area of intended skin rejuvenation via the channels in the skin created by the derma roller. Accordingly, the chemical compound is able to reach the dermis layer of the skin, directly underneath the epidermis, much faster than would be required through prolonged exposure to the chemical compound; as a result, collagen production is increased in an optimal manner to rejuvenate (i.e., tone, tighten, and/or lift) the skin. Finally, a red light therapy device is utilized to emit red light (i.e., light having a wavelength of six hundred ten nanometers to seven hundred nanometers) toward the area of intended rejuvenation, which further increases collagen production.

Accordingly, the positioning of the chemical compound within the channels created by derma roller, combined with the sequential step of red light emission toward the area of intended rejuvenation, has been discovered to have an enhanced collagen production effect that mimics plastic surgery results.

Furthermore, the same three-step process may be utilized in a universal manner with respect to various portions of the face to mimic plastic surgery results corresponding to different plastic surgery procedures (e.g., face lift, jaw lift, etc.), but with the same process. In other words, one process may be utilized in different zones of the face of a user to mimic plastic surgery results that would typically require different plastic surgery procedures, associated with potentially different visits to a plastic surgeon's office.

Additionally, in one embodiment, the three-step process may be utilized to simultaneously mimic the results from multiple plastic surgery procedures during one application. For example, the user may apply the derma roller to both the skin around the eyes and the skin around the jaw during one application, followed by application of retinol to the skin around the eyes and the skin around the jaw, and followed by red light therapy emission to the skin around the eyes and the skin around the jaw. Accordingly, the three-step process allows a user to simultaneously mimic plastic surgery results corresponding to multiple plastic surgery procedures at the same time, and by using the same process, without necessitating any variation thereto.

Figure 4A:
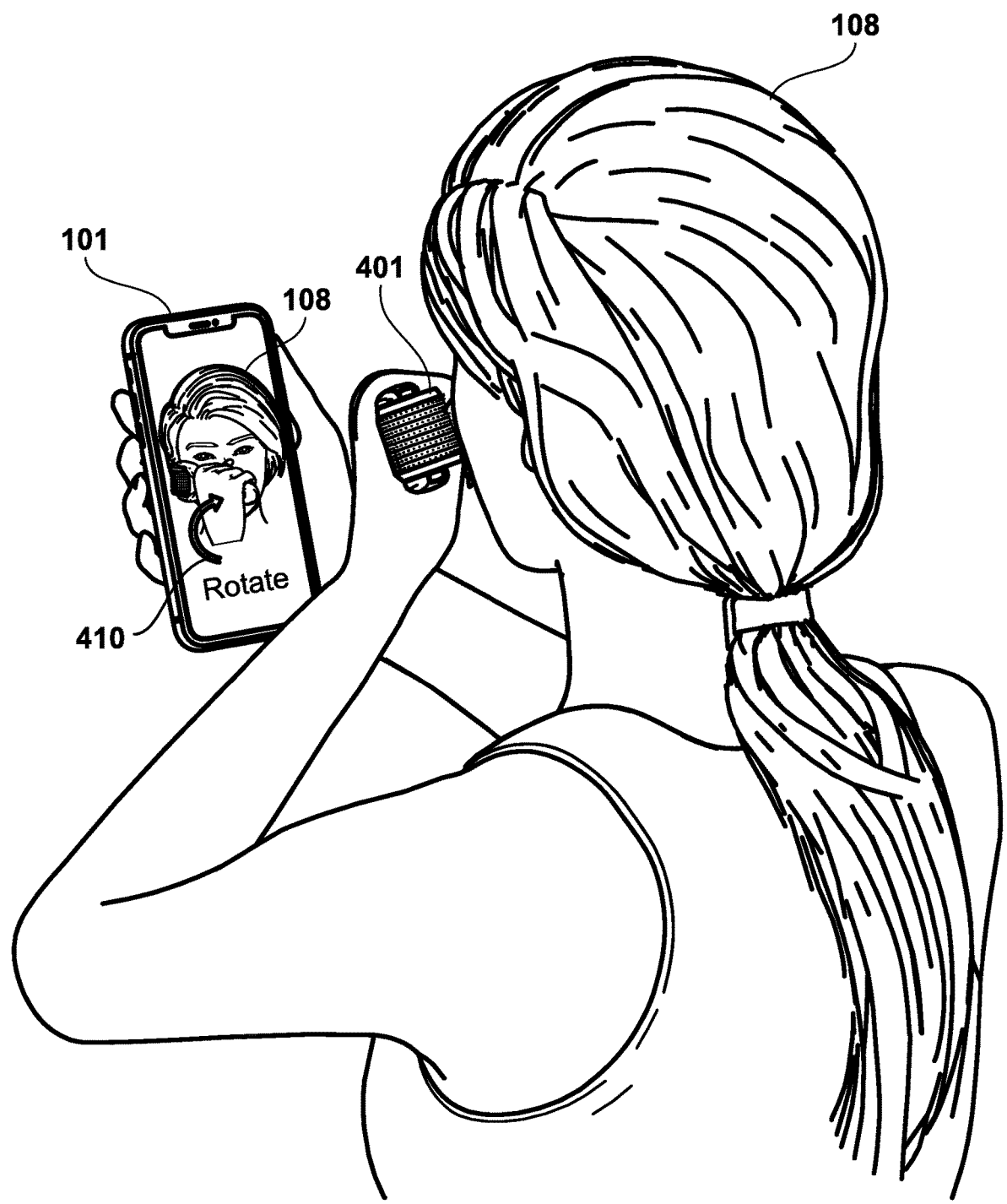
FIG. 4A illustrates the user performing the first step of the three-step process incorrectly, and the software configuration providing one or more virtual cues for the user 108 to perform this step correctly.
Figure 4B:
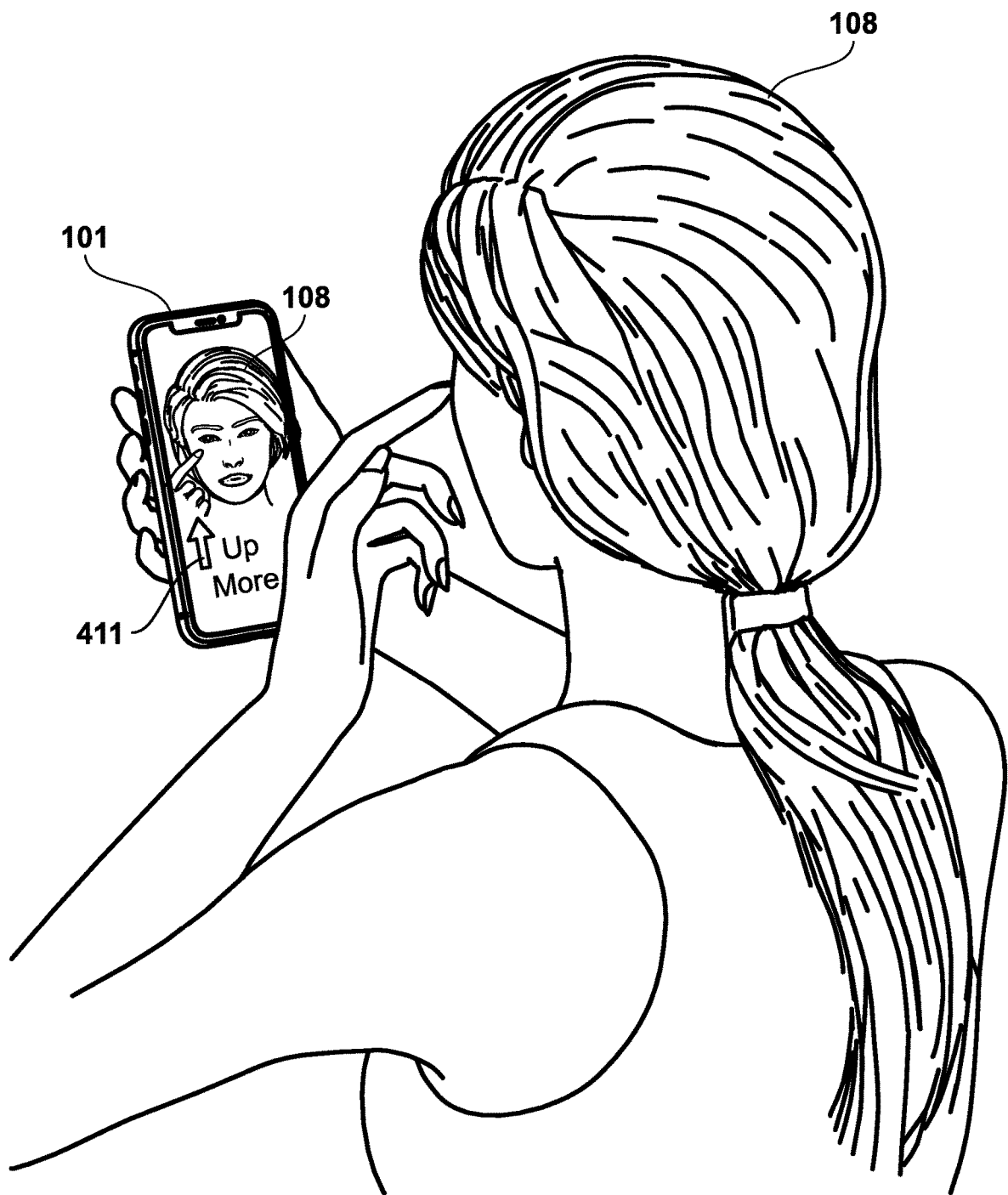
FIG. 4B illustrates the user performing the second step of the three-step process incorrectly.
Figure 4C:
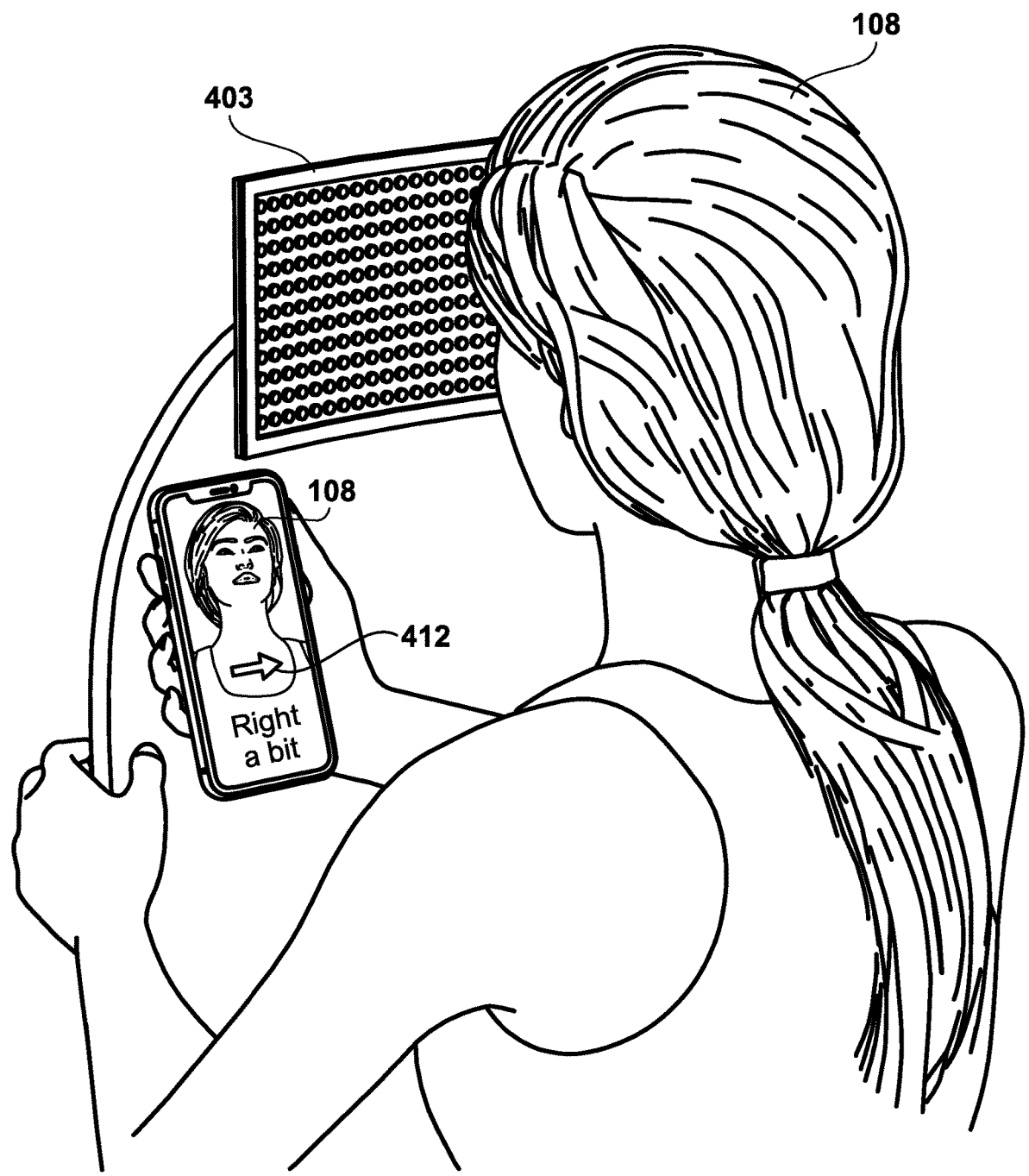
FIG. 4C illustrates the user adjusting a red light therapy emission device in a manner that does not optimally emit red light therapy toward the intended area of rejuvenation.

FIGS. 4A-4C illustrate the user 108 utilizing the three-step process in conjunction with the software configuration. In particular, FIG. 4A illustrates the user 108 performing the first step of the three-step process incorrectly, and the software configuration providing one or more virtual cues 410 for the user 108 to perform this step correctly. In this example, the user 108 should be moving the derma roller 401 in a vertical motion, but instead is moving it in a horizontal motion. Accordingly, the software configuration depicts a virtual cue 410 in the form of an arrow to alert the user 108 to adjust the movement of the derma roller 401. (An arrow is just one example of a visual-based virtual cue. Additionally, or alternatively, audio-based cues may be utilized.) Furthermore, FIG. 4B illustrates the user 108 performing the second step of the three-step process incorrectly. For example, the user 108 may apply the chemical compound outside of a predefined area 420 (e.g., a four inch by four inch patch) that surrounds the intended area of rejuvenation, but that predefined area is an optimal area for skincare rejuvenation. Accordingly, a virtual cue 411 may direct the user 108 to apply the chemical compound within the predefined area 420. Finally, FIG. 4C illustrates the user 108 adjusting a red light therapy emission device 403 in a manner that does not optimally emit red light therapy toward the intended area of rejuvenation. The software configuration generates a virtual cue 412 to direct the user 108 to adjust the red light therapy machine to perform optimal emissions toward the user 108.

Figure 5:
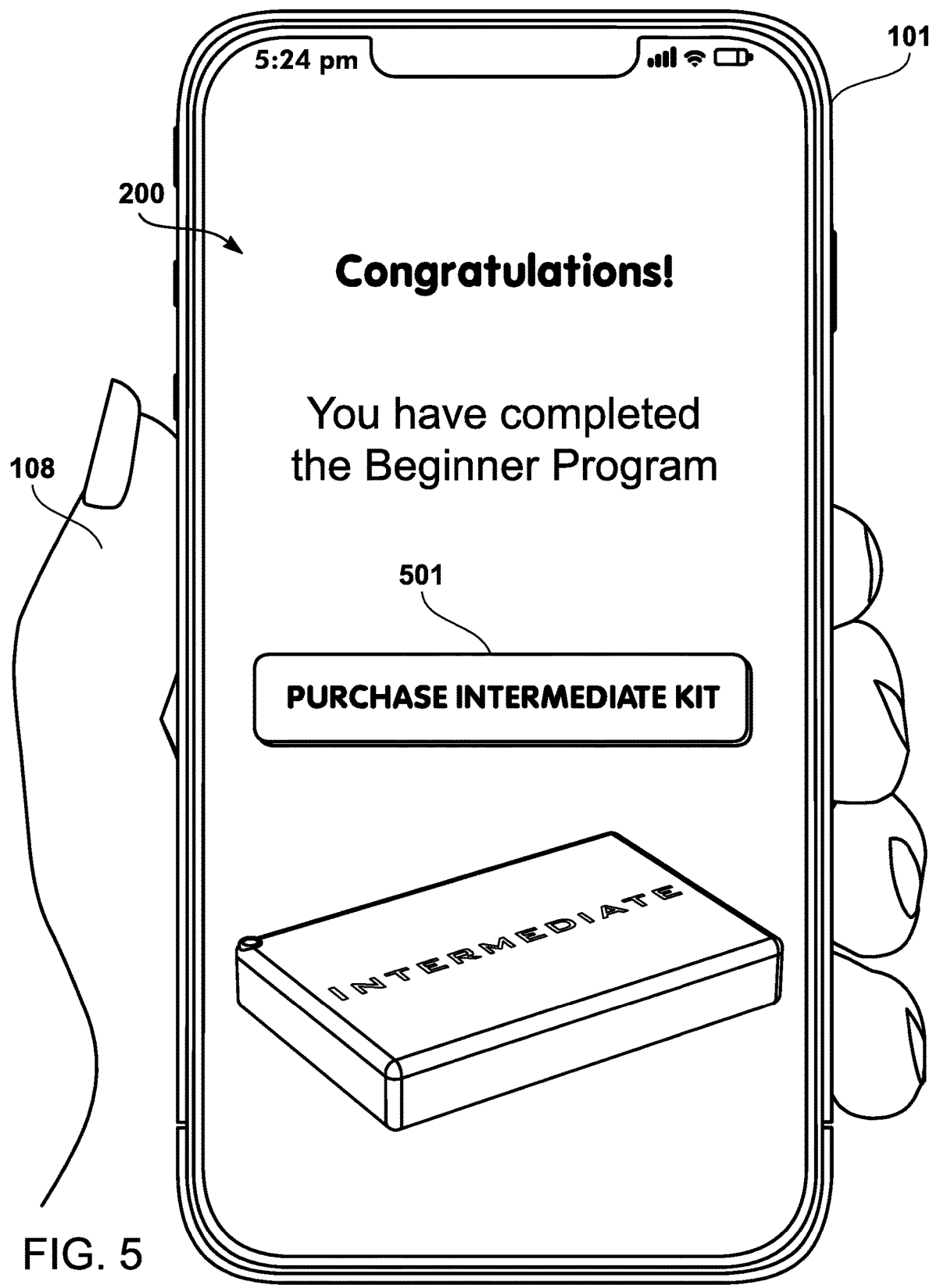
FIG. 5 illustrates an example of the GUI with a kit/product purchase indicium.

FIG. 5 illustrates an example of the GUI 200 with a kit/product purchase indicium 501. Upon meeting a milestone, such as reaching or exceeding an improvement threshold, the software configuration may automatically present the kit/product purchase indicium 501 via the GUI 200. As a result, the user 108 may select the kit/product purchase indicium 501 to be redirected to a website to purchase the kit and/or product. In an alternative embodiment, the user 108 may purchase the kit or product directly from the software app 115.

Figure 6:
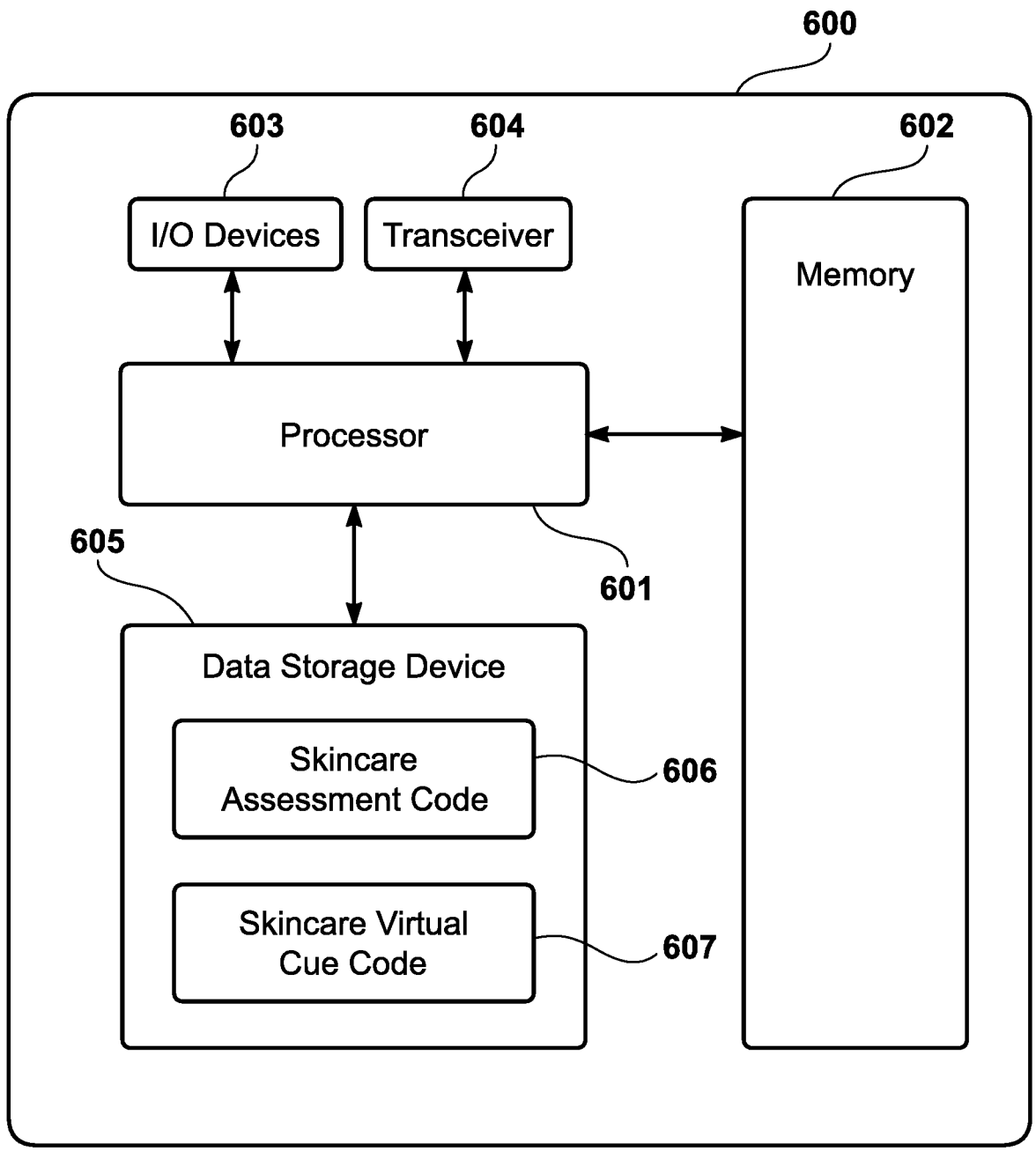
FIG. 6 illustrates a system configuration for the skincare app server illustrated in FIG. 1.

FIG. 6 illustrates a system configuration for the skincare app server 105 illustrated in FIG. 1. The skincare app server 105 may have a processor 601, which may be specialized for skincare assessment and skincare virtual cue generation. Accordingly, the processor 601 may be used to perform the operations illustrated in FIG. 1 for performing image analysis on the skin of the user to determine skincare improvement efficacy.

The system configuration may also include a memory device 602, which may temporarily store images from the image database 110, illustrated in FIG. 1, for improved processing times by the processor 601. As a result, the skincare app 115 is able to provide real-time (measured as an imperceptible time delay), or substantially real-time (measured as a perceptible time delay that is generally acceptable to the user 108 (e.g., one to two seconds)), skincare assessment and/or skincare cue generation. Furthermore, the memory device 602 may store computer readable instructions performed by the processor 601. As an example of such computer readable instructions, a data storage device 605 within the system configuration may store skincare assessment code 606 and skincare virtual cue code 607. The processor 601 may execute the skincare assessment code 606 to invoke a virtual skincare assessment. Furthermore, the processor 601 may execute skincare virtual code 608 to invoke skincare virtual cues.

Moreover, the system configuration may have one or more input/output ("I/O") devices 603 that may receive inputs and provide outputs. Various devices (e.g., image capture devices, keyboard, microphone, mouse, pointing device, hand controller, joystick, display device, holographic projector, etc.) may be used for the I/O devices 603. The system configuration may also have a transceiver 604 to send and receive data. Alternatively, a separate transmitter and receiver may be used instead.

Figure 7:
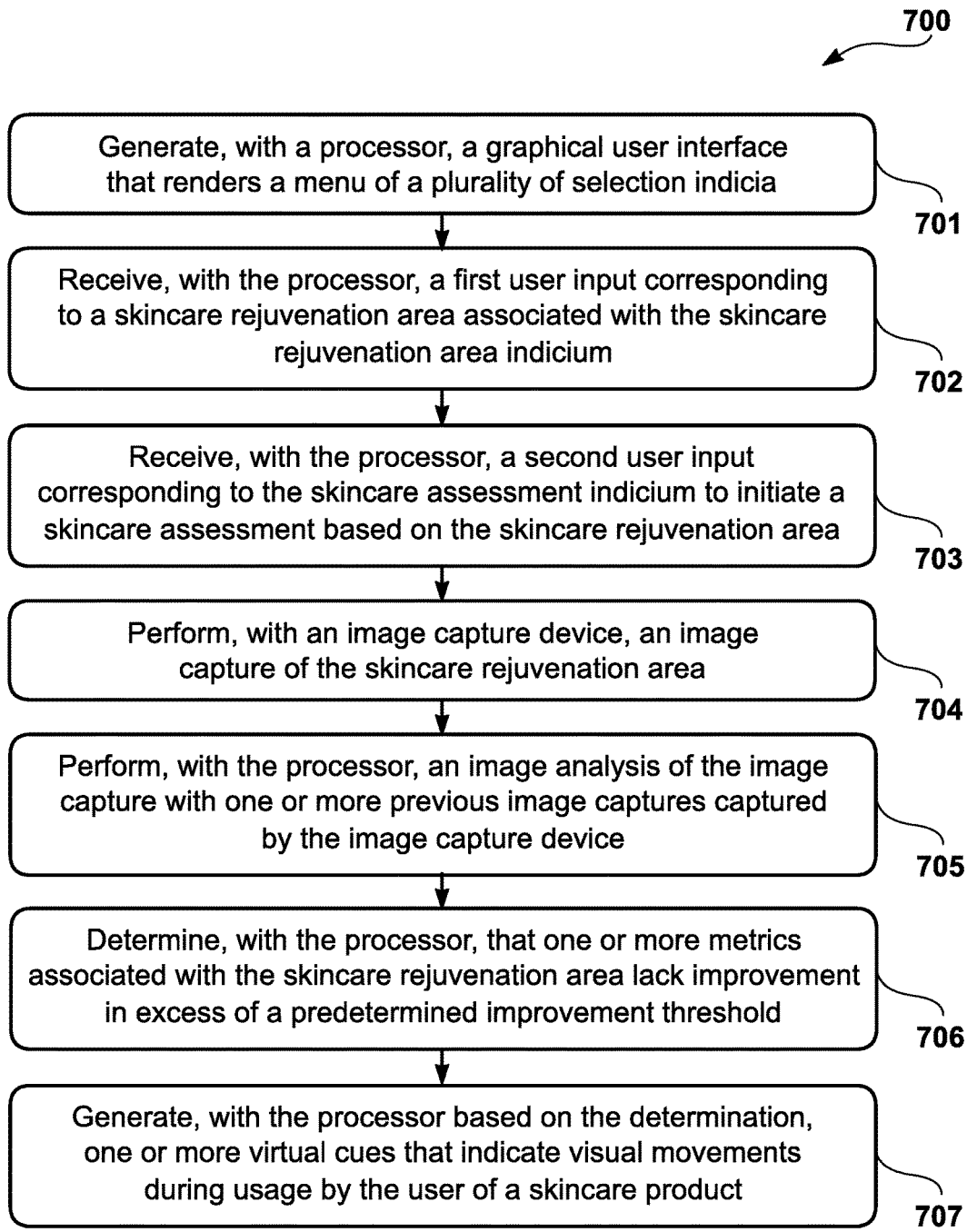
FIG. 7 illustrates a process that may be utilized by the skincare app server.

FIG. 7 illustrates a process 700 that may be utilized by the skincare app server 105. At a process block 701, the process 700 generates, with a processor 601, a GUI that renders a menu of a plurality of selection indicia. The plurality of selection indicia includes a skincare rejuvenation area indicium, a skincare assessment indicium, and a skincare interactive cue indicium. Furthermore, at a process block 702, the process 700 receives, with the processor 601, a first user input corresponding to a skincare rejuvenation area associated with the skincare rejuvenation area indicium. Additionally, at a process block 703, the process receives, with the processor 601, a second user input corresponding to the skincare assessment indicium to initiate a skincare assessment based on the skincare rejuvenation area. At a process block 704, the process 700 performs, with an image capture device 102, an image capture of the skincare rejuvenation area. Furthermore, at a process block 705, the process 700 performs, with the processor 601, an image analysis of the image capture with one or more previous image captures captured by the image capture device. Additionally, at a process block 706, the process 700 determines, with the processor 601, that one or more metrics associated with the skincare rejuvenation area lack improvement in excess of a predetermined improvement threshold. Finally, at a process block 707, the process 700 generates, with the processor 601 based on the determination, one or more virtual cues that indicate visual movements during usage by the user of a skincare treatment process. The virtual cues are overlaid over an image of the user displayed by the graphical user interface.

It is understood that the processes, systems, apparatuses, and computer program products described herein may also be applied in other types of processes, systems, apparatuses, and computer program products. Those skilled in the art will appreciate that the various adaptations and modifications of the embodiments of the processes, systems, apparatuses, and computer program products described herein may be configured without departing from the scope and spirit of the present processes and systems. Therefore, it is to be understood that, within the scope of the appended claims, the present processes, systems, apparatuses, and computer program products may be practiced other than as specifically described herein.

I claim:

1. A computer program product comprising a non-transitory computer readable storage device having a computer readable program stored thereon, wherein the computer readable program when executed on a computer causes the computer to:

generate, with a processor, a graphical user interface that renders a menu of a plurality of selection indicia, the plurality of selection indicia including a skincare rejuvenation area indicium, a skincare assessment indicium, and a skincare interactive cue indicium;

receive, with the processor, a first user input corresponding to a skincare rejuvenation area associated with the skincare rejuvenation area indicium, wherein the processor prompts for the first user input corresponding to the skincare rejuvenation area at a predetermined time interval, and wherein the processor prevents receipt of the first user input corresponding to the skincare rejuvenation area until the predetermined time interval;

receive, with the processor, a second user input corresponding to the skincare assessment indicium to initiate a skincare assessment based on the skincare rejuvenation area;

perform, with an image capture device, an image capture of the skincare rejuvenation area;

filter out, with the processor, one or more portions of the image capture that have improved over a predetermined improvement threshold to identify one or more remaining portions of the image capture, wherein the predetermined improvement threshold varies based on the received skincare rejuvenation area due to at least two changes in discoloration, opacity, density and pore size of corresponding pixels;

perform, with the processor, an image analysis of the one or more remaining portions of the image capture with one or more previous image captures captured by the image capture device, wherein the performed image analysis of the one or more remaining portions of the image capture delivers a faster result as compared to an image analysis of all portions of the image capture;

determine, with the processor, that one or more metrics associated with the skincare rejuvenation area lack improvement in excess of the predetermined improvement threshold for the skincare rejuvenation area; and generate, with the processor based on the determination, one or more virtual cues that indicate visual movements during usage by a user of a skincare treatment process wherein the virtual cues are overlaid over an image of the user displayed by the graphical user interface.

2. The computer program product of claim 1, wherein the computer is further caused to render a progression-based slider in the graphical user interface, the progression-based slider have a plurality of time-based indicia corresponding to time increments for the skincare assessment, at least a portion of the time increments each corresponding to at least one previous time at which a previous image capture of the skincare rejuvenation area was performed.

3. The computer program product of claim 2, wherein each of the time increments corresponds to the previous image capture and additional previous image captures as captured in sequence.

4. The computer program product of claim 3, wherein the computer is further caused to render the one or more metrics in proximity to the corresponding previous image within the graphical user interface.

5. The computer program product of claim 4, wherein the computer is further caused to dynamically modify the one or more metrics based on a position within the progression-based slider.

6. The computer program product of claim 5, wherein the one or more metrics are selected from the group consisting of eye wrinkle reduction, cheek wrinkle reduction, and facial pore reduction.

7. The computer program product of claim 1, wherein the skincare treatment process comprises:

performing, with a derma roller, a predetermined maximum number of movements in each of one or more predetermined directions along an area of intended rejuvenation of a face of a human user, wherein the predetermined maximum number of movements equals four, the derma roller having a head with a plurality of needles each having a length of five tenths millimeters situated thereon;

applying, subsequent to the derma roller performance, a chemical compound to one or more patches of skin at the area of intended rejuvenation, the one or more patches of skin each having a predetermined patch size, the chemical compound comprising vitamin $A_1$, the predetermined patch size equaling four inches in length by four inches in width; and emitting, subsequent to the application of the chemical compound, red light toward the area of intended rejuvenation for a minimum predetermined period of time of ten minutes, the red light having a wavelength in the range of six hundred ten nanometers to seven hundred nanometers.

8. The computer program product of claim 7, wherein the one or more visual cues are one or more directional indicia that visually guide the user in the performance with the derma roller to optimize the improvement to meet the predetermined improvement threshold.

9. The computer program product of claim 7, wherein the one or more visual cues are one or more pressure indicia that visually guide the user in pressure application during the performance with the derma roller.

10. The computer program product of claim 7, wherein the computer is further caused to determine, with the processor, that one or more metrics associated with the skincare rejuvenation area have improved in excess of a predetermined improvement threshold, the computer being further caused to display an efficacy indication based on the improvement of the one or more metrics.

11. The computer program product of claim 10, wherein the computer is further caused to automatically recommend an advancement through the skincare treatment system based on the improvement of the one or more metrics.

12. The computer program product of claim 11, wherein the computer is further caused to automatically render a hyperlink within the graphical interface based upon the improvement of the one or more metrics, the hyperlink being associated with a website at which one or more products associated the advancement is available for purchase.

13. The computer program product of claim 7, wherein the virtual cues further include one or more audio emissions that guide the user in the performance with the derma roller.

14. A computer-implemented skincare system:

a processor that establishes a software configuration that is accessible via a mobile computing device; and a skincare application server that is configured to:

receives, from the mobile computing device via the software configuration, a first user input corresponding to a skincare rejuvenation area associated with the skincare rejuvenation area indicium, wherein the processor prompts for the first user input corresponding to the skincare rejuvenation area at a predetermined time interval, and wherein the processor prevents receipt of the first user input corresponding to the skincare rejuvenation area until the predetermined time interval;

receives, from the mobile computing device via the software configuration, a second user input corresponding to the skincare assessment indicium to initiate a skincare assessment based on the skincare rejuvenation area;

receives, from the mobile computing device via the software configuration, an image capture of the skincare rejuvenation area, filter out, from the mobile computing device, one or more portions of the image capture that have improved over a predetermined improvement threshold to identify one or more remaining portions of the image capture, wherein the predetermined improvement threshold varies based on the received skincare rejuvenation area due to at least two changes in discoloration, opacity, density and pore size of corresponding pixels;

performs, with the processor, an image analysis of the one or more remaining portions of the image capture with one or more previous image captures captured by the image capture device, wherein the performed image analysis of the one or more remaining portions of the image capture delivers a faster result as compared to an image analysis of all portions of the image capture, determines, with the processor, that one or more metrics associated with the skincare rejuvenation area lack improvement in excess of the predetermined improvement threshold for the skincare rejuvenation area; and generates, with the processor based on the determination, one or more virtual cues that indicate visual movements during usage by a user of a skincare treatment process wherein the virtual cues are overlaid over an image of the user displayed by the graphical user interface.

15. The computer-implemented skincare system of claim 14, wherein the software configuration renders a progression-based slider in the graphical user interface, the progression-based slider have a plurality of time-based indicia corresponding to time increments for the skincare assessment, at least a portion of the time increments each corresponding to at least one previous time at which a previous image capture of the skincare rejuvenation area was performed.

16. The computer-implemented skincare system of claim 15, wherein each of the time increments corresponds to the previous image capture and additional previous image captures as captured in sequence.

17. The computer-implemented skincare system of claim 16, wherein the software configuration renders the one or more metrics in proximity to the corresponding previous image within the graphical user interface.

18. The computer-implemented skincare system of claim 17, wherein the software configuration dynamically modifies the one or more metrics based on a position within the progression-based slider.

* * * * *